ns011474032B2

(12) United States Patent
Sugiura et al.

(10) Patent No.: US 11,474,032 B2
(45) Date of Patent: Oct. 18, 2022

(54) SCALE COMPOSITION DETERMINATION SYSTEM, SCALE COMPOSITION DETERMINATION METHOD, AND PROGRAM

(71) Applicant: NIPPON STEEL CORPORATION, Tokyo (JP)

(72) Inventors: Masato Sugiura, Tokyo (JP); Hiroshi Tanei, Tokyo (JP); Shuichi Yamazaki, Tokyo (JP); Yasumitsu Kondo, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 699 days.

(21) Appl. No.: 16/484,615

(22) PCT Filed: Apr. 25, 2018

(86) PCT No.: PCT/JP2018/016865
§ 371 (c)(1),
(2) Date: Aug. 8, 2019

(87) PCT Pub. No.: WO2018/199187
PCT Pub. Date: Nov. 1, 2018

(65) Prior Publication Data
US 2020/0033268 A1 Jan. 30, 2020

(30) Foreign Application Priority Data
Apr. 25, 2017 (JP) .............................. JP2017-086174

(51) Int. Cl.
*G01N 21/35* (2014.01)
*G01N 33/20* (2019.01)
(Continued)

(52) U.S. Cl.
CPC ......... *G01N 21/3563* (2013.01); *G01N 21/71* (2013.01); *G01N 33/2028* (2019.01)

(58) Field of Classification Search
CPC . G01N 21/71; G01N 21/3563; G01N 33/2028
(Continued)

(56) References Cited

U.S. PATENT DOCUMENTS 4,759,072 A * 7/1988 Yamane ................. G01N 21/89
250/559.46
5,235,840 A 8/1993 Blazevic
(Continued)

FOREIGN PATENT DOCUMENTS

JP 8-219891 A 8/1996
JP 9-33464 A 2/1997
(Continued)

OTHER PUBLICATIONS

Zanzucchi, P. J. et al, Applied Spectroscopy 1986, 40, 1042-1046.*
(Continued)

*Primary Examiner* — Arlen Soderquist
(74) *Attorney, Agent, or Firm* — Birch, Stewart, Kolasch & Birch, LLP

(57) ABSTRACT

A scale composition determination device (10) determines that $Fe_2O_3$ has been generated in the outermost layer of a scale (SC) in the case where at least one of spectral emissivities at one wavelength and the other wavelength that are measured by radiometers for spectral emissivity measurement (21a, 21b) is not within a predetermined range including spectral emissivities of FeO at one wavelength and the other wavelength, and determines that $Fe_2O_3$ has not been generated in the outermost layer of the scale (SC) in the case where all of the spectral emissivities at one wavelength and the other wavelength that are measured by the radiometers for spectral emissivity measurement (21a, 21b) is within the
(Continued)

predetermined range including the spectral emissivities of FeO at one wavelength and the other wavelength.

4 Claims, 8 Drawing Sheets

(51) Int. Cl.
  *G01N 21/71* (2006.01)
  *G01N 21/3563* (2014.01)
  *G01N 33/2028* (2019.01)
(58) Field of Classification Search
  USPC .......................................................... 436/78
  See application file for complete search history.

(56) References Cited

U.S. PATENT DOCUMENTS

| | | | | |
|---|---|---|---|---|
| 5,314,249 | A * | 5/1994 | Marui | G01J 5/60 |
| | | | | 374/128 |
| 11,029,212 | B2 * | 6/2021 | Tanei | G01J 5/0003 |
| 2005/0063451 | A1 * | 3/2005 | Abe | G02B 7/1815 |
| | | | | 374/121 |
| 2015/0226610 | A1 * | 8/2015 | Uematsu | G01J 5/0003 |
| | | | | 250/338.3 |
| 2018/0283849 | A1 * | 10/2018 | Fricout | G01B 11/0625 |
| 2020/0103285 | A1 * | 4/2020 | Tanei | G01J 5/0003 |
| 2021/0247235 | A1 * | 8/2021 | Tanei | G01J 5/0022 |

FOREIGN PATENT DOCUMENTS

| | | | |
|---|---|---|---|
| JP | 2002-53987 | * | 2/2002 |
| JP | 2012-93177 A | | 5/2012 |
| JP | 2014-55830 A | | 3/2014 |
| JP | 2017-156270 A | | 9/2017 |
| WO | WO 95/13149 A1 | | 5/1995 |
| WO | WO 2013/035726 A1 | | 3/2013 |
| WO | WO 2017/056061 A1 | | 4/2017 |

OTHER PUBLICATIONS

Tierney, M. et al., SPIE 1990, 1320, 257-261.*
Torres, M. et al, Journal of Materials Processing Technology 2000, 105, 258-263.*
Avdelidis, N. P. et al, Energy and Buildings 2003, 35, 663-667.*
Del Campo, L. et al, Corrosion Science 2008, 50, 194-199.*
Yazdchi, M. R. et al, 2008 International Conference on Computational Intelligence for Modelling Control & Automation 2008, 1071-1076.*
Jang, J. H. et al, International Journal of Heat and Mass Transfer 2010, 53, 4326-4332.*
Sidelev, A., Dissertation 2011, 156 pages.*
Graf, M. et al, La Metallurgia Italiana 2014, 43-49.*
Wiskel, J. B. QIRT 2014, 7 pages, downloaded from http://www.qirt.org/archives/qirt2014/QIRT%202014%20Papers/QIRT-2014-004.pdf.*
Ham, S. H. QIRT 2016, 7 pages, downloaded from http://www.qirt.org/archives/qirt2016/papers/041.pdf.*
Larciprete, M. C. et al, International Journal of Thermal Sciences 2017, 113, 130-135.*
International Search Report for PCT/JP2018/016865 dated Jul. 31, 2018.
Written Opinion of the International Searching Authority for PCT/JP2018/016865 (PCT/ISA/237) dated Jul. 31, 2018.
International Preliminary Report on Patentability and English translation of the Written Opinion of the International Searching Authority (Forms PCT/IB/326, PCT/IB/373, and PCT/ISA/237) for corresponding International Application No. PCT/JP2018/016865, dated Nov. 7, 2019.

* cited by examiner

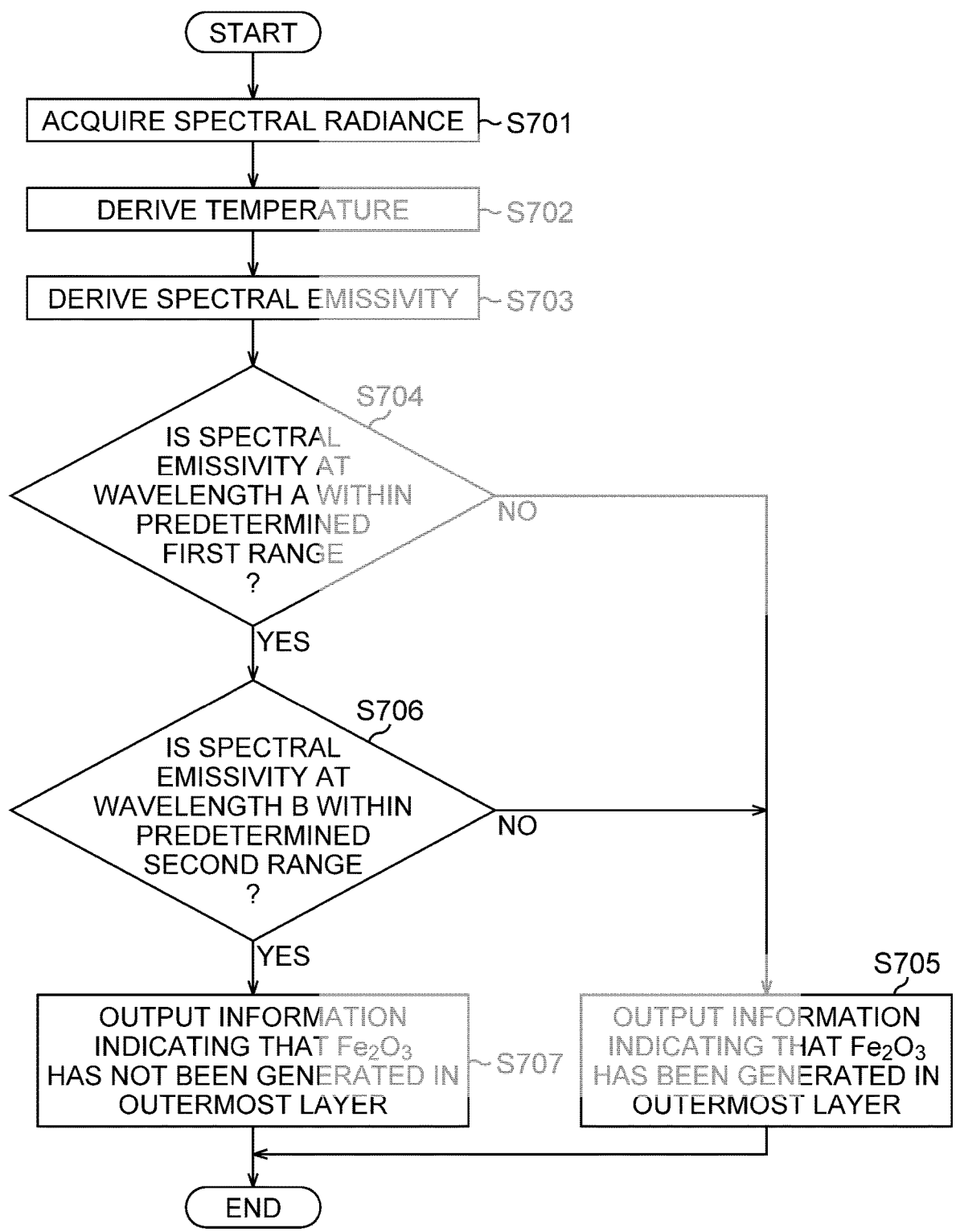

SCALE COMPOSITION DETERMINATION SYSTEM, SCALE COMPOSITION DETERMINATION METHOD, AND PROGRAM

TECHNICAL FIELD

The present invention relates to a scale composition determination system, a scale composition determination method, and a program, and is suitably used for determining the composition of a scale generated on a surface of a steel material, in particular.

BACKGROUND ART

As described in Patent Literature 1, when a steel material is heated, a scale (layer of iron oxide) is generated on its surface. In a step of hot rolling the steel material, for example, the red-hot steel material at 600[° C.] to 1200[° C.] is drawn by rollers while being conveyed on a line. Thus, on the surface of the steel material during hot rolling, a scale is always generated. As for the scale, there are three types of composition of wustite (FeO), magnetite ($Fe_3O_4$), and hematite ($Fe_2O_3$).

The adhesiveness of a scale has something to do with its composition. A multilayer scale having $Fe_2O_3$ generated in the outermost layer of a scale is likely to exfoliate. On the other hand, a single-layer scale having a scale composition of only FeO is high in adhesiveness.

Thus, the scale that is likely to exfoliate when passing through a scale removing device called a descaler is preferred. Conversely, when a pattern resulting from uneven exfoliation of the scale becomes a problem in terms of quality of the surface, the scale is preferably in close contact with the steel material. Thus, it is desired to determine the composition of the scale and use a determination result for operation.

As a method of determining the composition of a scale, X-ray diffraction measurement is considered. In the X-ray diffraction measurement, a test piece obtained by cutting a steel material with a growing scale thereon into a size of about several centimeters is fabricated and an X-ray diffraction pattern of this test piece is measured. X-ray diffraction patterns different according to a crystal structure of the scale are obtained. Thus, the X-ray diffraction pattern makes it possible to determine whether or not $Fe_2O_3$ is present in the outermost layer of the scale (namely, the scale is the previously described single-layer scale or multilayer scale).

However, the X-ray diffraction measurement requires fabrication of a test piece by cutting the steel material. Moreover, the X-ray diffraction pattern can be measured only after the steel material is cooled. Thus, it is impossible to determine the composition of a scale generated on the surface of the steel material during operation online (in real time).

Thus, the art described in Patent Literature 1 determines whether or not $Fe_2O_3$ is present in the outermost layer of a scale by determining which of a process of supplying oxygen molecules to an oxide film on the surface of a steel sheet or a process of iron atoms oxidizing on the surface of a steel material determines the rate of a rate-determining process of oxidation on the surface of the steel material.

CITATION LIST

Patent Literature

Patent Literature 1: Japanese Laid-open Patent Publication No. 2012-93177

SUMMARY OF INVENTION

Technical Problem

However, the art described in Patent Literature 1 needs to use a model equation in order to determine the rate-determining process of oxidation on the surface of the steel material. Thus, the accuracy of determination relies on the accuracy of the model equation. Further, in a hot rolling line, descalers spray high-pressure water on the steel sheet. Consequently, water or water vapor is present partially on the surface of the steel sheet on the hot rolling line. Therefore, there is a case that an oxygen supply process necessary for model calculation is not confirmed correctly. As above, the art described in Patent Literature 1 causes a problem that it is not easy to accurately determine the composition of a scale generated on the surface of the steel material during operation online (in real time).

The present invention has been made in consideration of the above problems, and an object thereof is to be capable of accurately determining the composition of a scale generated on the surface of a steel material during operation online.

Solution to Problem

A scale composition determination system of the present invention is a scale composition determination system that determines a composition of a scale generated on a surface of a steel material, the scale composition determination system including: a detection means that detects spectral radiance of the steel material at each of a plurality of wavelengths; a temperature acquisition means that acquires a temperature of the steel material; a spectral emissivity deriving means that derives spectral emissivity of the steel material at each of a plurality of the wavelengths based on the temperature of the steel material acquired by the temperature acquisition means and the spectral radiance of the steel material at each of a plurality of the wavelengths, the spectral radiance detected by the detection means; and a determination means that determines whether or not hematite ($Fe_2O_3$) has been generated in an outermost layer of the scale based on the spectral emissivity of the steel material at each of a plurality of the wavelengths, the spectral emissivity derived by the spectral emissivity deriving means, in which the determination means determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths, in the predetermined range set at the wavelength, spectral emissivity of wustite (FeO) at the corresponding wavelength is included, a plurality of the wavelengths are determined by using the relationship between the spectral emissivity of the hematite at each of a plurality of the wavelengths and a thickness of the hematite within a range assumed as the thickness of the hematite, and a plurality of the wavelengths are determined to make the spectral emissivity of the hematite at at least one wavelength of a plurality of the wavelengths fall outside the predetermined range set at the corresponding wavelength at any thickness of the hematite in the relationship.

A scale composition determination method of the present invention is a scale composition determination method that determines a composition of a scale generated on a surface of a steel material, the scale composition determination method including: a detection step of detecting spectral radiance of the steel material at each of a plurality of wavelengths; a temperature acquisition step of acquiring a temperature of the steel material; a spectral emissivity deriving step of deriving spectral emissivity of the steel material at each of a plurality of the wavelengths based on the temperature of the steel material acquired by the temperature acquisition step and the spectral radiance of the steel material at each of a plurality of the wavelengths, the spectral radiance detected by the detection step; and a determination step of determining whether or not hematite ($Fe_2O_3$) has been generated in an outermost layer of the scale based on the spectral emissivity of the steel material at each of a plurality of the wavelengths, the spectral emissivity derived by the spectral emissivity deriving step, in which the determination step determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths, in the predetermined range set at the wavelength, spectral emissivity of wustite (FeO) at the corresponding wavelength is included, a plurality of the wavelengths are determined by using the relationship between the spectral emissivity of the hematite at each of a plurality of the wavelengths and a thickness of the hematite within a range assumed as the thickness of the hematite, and a plurality of the wavelengths are determined to make the spectral emissivity of the hematite at at least one wavelength of a plurality of the wavelengths fall outside the predetermined range set at the wavelength at any thickness of the hematite in the relationship.

A program of the present invention is a program for causing a computer to execute determination of a composition of a scale generated on a surface of a steel material, the program causing a computer to execute: a spectral emissivity deriving step of deriving spectral emissivity of the steel material at each of a plurality of wavelengths based on a temperature of the steel material and spectral radiance of the steel material at each of a plurality of the wavelengths; and a determination step of determining whether or not hematite ($Fe_2O_3$) has been generated in an outermost layer of the scale based on the spectral emissivity of the steel material at each of a plurality of the wavelengths, the spectral emissivity derived by the spectral emissivity deriving step, in which the determination step determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths, in the predetermined range set at the wavelength, spectral emissivity of wustite (FeO) at the corresponding wavelength is included, a plurality of the wavelengths are determined by using the relationship between the spectral emissivity of the hematite at each of a plurality of the wavelengths and a thickness of the hematite within a range assumed as the thickness of the hematite, and a plurality of the wavelengths are determined to make the spectral emissivity of the hematite at at least one wavelength of a plurality of the wavelengths fall outside the predetermined range set at the wavelength at any thickness of the hematite in the relationship.

BRIEF DESCRIPTION OF DRAWINGS

FIG. 7 is a flowchart explaining one example of an operation of a scale composition determination device.

DESCRIPTION OF EMBODIMENTS

Hereinafter, there will be explained one embodiment of the present invention with reference to the drawings.

<Outline of a Configuration of a Hot Rolling Line>

Figure 1:
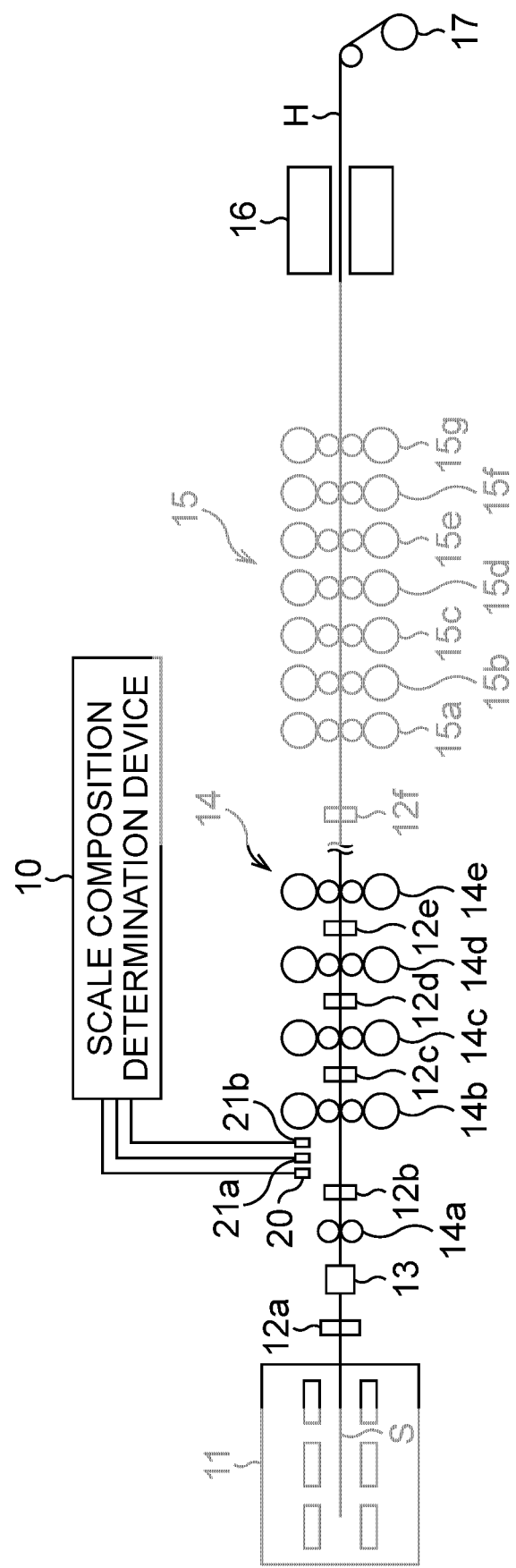
FIG. 1 is a view illustrating one example of a schematic configuration of a hot rolling line.

FIG. 1 is a view illustrating one example of a schematic configuration of a hot rolling line being one example of an application destination of a scale composition determination device 10.

In FIG. 1, the hot rolling line has a heating furnace 11, descalers 12a to 12f, a width-direction mill 13, a roughing mill 14, a finishing mill 15, a cooling device (run out table) 16, and a coiling device (coiler) 17.

The heating furnace 11 heats a slab (steel material) S.

The descalers 12a to 12f remove a scale generated on the surface of the steel material. The thickness of the scale is 10 [µm] to 100 [µm], for example. The descalers 12a to 12f spray, for example, pressurized water on the surface of the steel material, thereby performing descaling (removing the scale). Incidentally, the steel material is high in temperature, so that the steel material is immediately oxidized again even though the scale is removed. Thus, the steel material is rolled in a state where a scale is always present on the surface.

The width-direction mill 13 rolls the slab S heated in the heating furnace 11 in the width direction.

The roughing mill 14 vertically rolls the slab S rolled in the width direction by the width-direction mill 13 to make a rough bar. In the example illustrated in FIG. 1, the roughing mill 14 has a rolling stand 14a composed of only work rolls and rolling stands 14b to 14e having work rolls and backup rolls.

The finishing mill 15 further continuously hot finishing rolls the rough bar manufactured by the roughing mill 14 to a predetermined thickness. In the example illustrated in FIG. 1, the finishing mill 15 has seven rolling stands 15a to 15g.

The cooling device 16 cools a hot-rolled steel sheet H hot finishing rolled by the finishing mill 15 by cooling water.

The coiling device 17 coils the hot-rolled steel sheet H cooled by the cooling device 16 into a coil shape.

Incidentally, the hot rolling line can be fabricated by a well-known art and is not limited to the configuration illustrated in FIG. 1. The descaler may be arranged between the upstream rolling stands (for example, between the rolling stands 15a and 15b and between the rolling stands 15b and 15c) out of the seven rolling stands 15a to 15g of the finishing mill 15, for example.

In this embodiment, at least one set of radiometers, which is one set composed of three radiometers, is arranged in the hot rolling line. Further, the three radiometers each detect spectral radiance of the steel material in a non-contact manner. However, one of the three radiometers is a radiometer to be used for measuring the temperature of the steel material by radiation thermometry. The remaining two of the three radiometers are radiometers to be used for measuring the spectral emissivity of the steel material.

Spectral radiance $L_b(\lambda, T)$ emitted by a blackbody with the absolute temperature T is expressed by (1) Equation below by Planck's law of blackbody radiation. Incidentally, the spectral radiance is a radiant flux [W·µm$^{-1}$·sr$^{-1}$·m$^{-2}$] per unit wavelength, per unit area, and per unit solid angle at a wavelength $\lambda$ [µm].

[Mathematical equation 1]

[Mathematical equation 1]

$$L_b(\lambda, T) = \frac{2c_1}{\lambda^5} \frac{1}{\exp\left(\frac{c_2}{\lambda T}\right) - 1} \quad (1)$$

Here, $c_1$ and $c_2$ are the first constant and the second constant for Planck's formula of blackbody radiation respectively.

(1) Equation represents the spectral radiance of the blackbody being an ideal radiator. Spectral radiance $L(\lambda, T)$ of an actual object is smaller than the spectral radiance $L_b(\lambda, T)$ of the blackbody at the same temperature. Thus, spectral emissivity $\varepsilon(\lambda, T)$ of an object to be measured is defined by (2) Equation below.

[Mathematical equation 2]

[Mathematical equation 2]

$$\varepsilon(\lambda, T) = \frac{L(\lambda, T)}{L_b(\lambda, T)} \quad (2)$$

In order to measure the spectral emissivity $\varepsilon(\lambda, T)$ as above, the spectral radiance $L(\lambda, T)$ of the object to be measured is measured. Further, the temperature T of the object to be measured is obtained in some way. Then, calculation of (2) Equation is performed using the spectral radiance $L(\lambda, T)$ of the object to be measured and the temperature T of the object to be measured.

In the example illustrated in FIG. 1, the case where a set of radiometers 20, 21a, and 21b is arranged in a region between the descaler 12b and the rolling stand 14b is illustrated. The rolling stand 14b is a rolling stand provided on the most upstream side out of the rolling stands having work rolls and backup rolls. Here, the radiometer 20 is set to be a radiometer to be used for measuring the temperature of the steel material. Further, the radiometers 21a, 21b are set to be radiometers to be used for measuring the spectral emissivity of the steel material.

Figure 2:
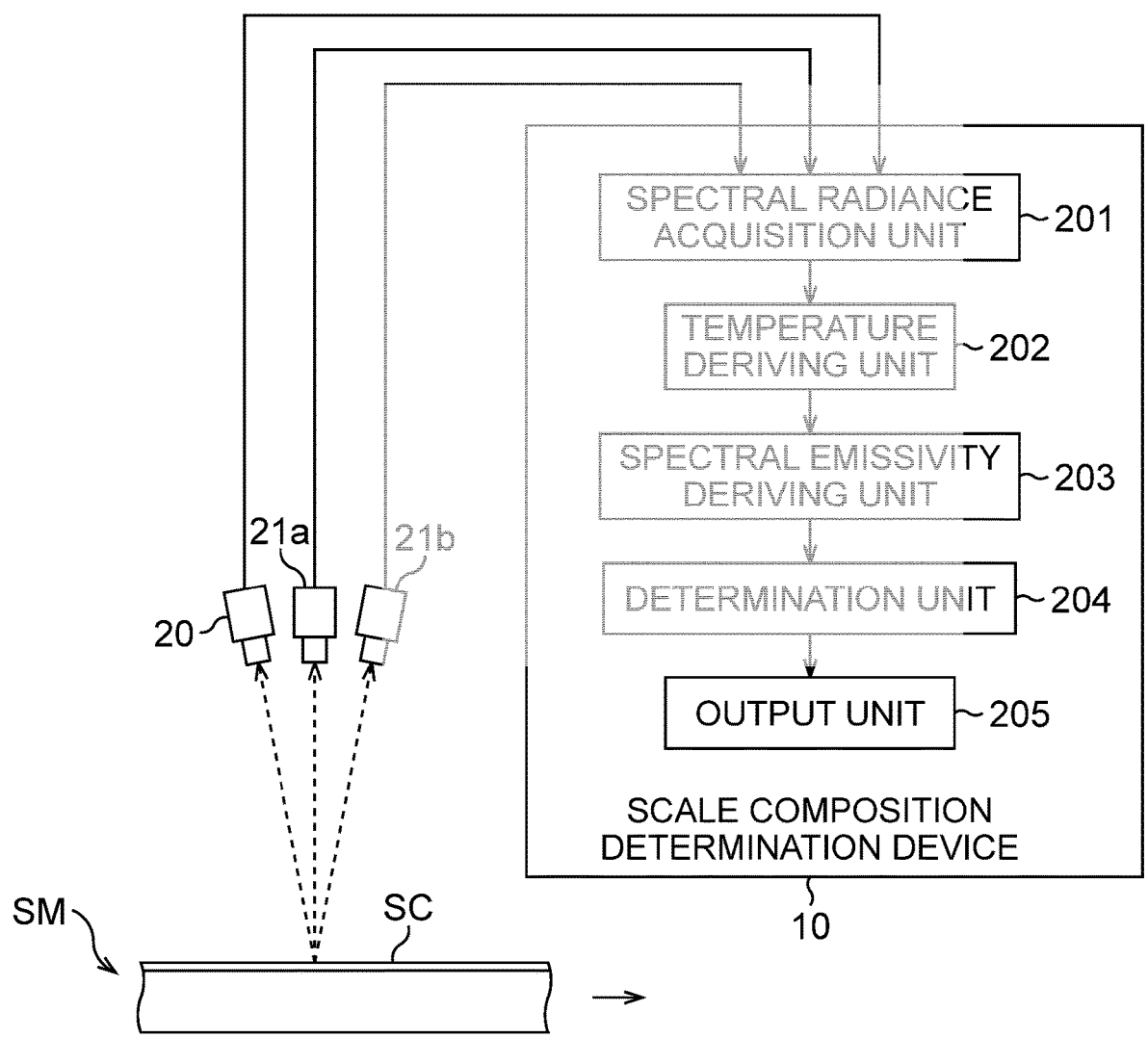
FIG. 2 is a view illustrating one example of a configuration of a scale composition determination system.

FIG. 2 is a view illustrating one example of a configuration of a scale composition determination system. In FIG. 2, examples of the arrangement of the radiometers 20, 21a, and 21b and a functional configuration of the scale composition determination device 10 are illustrated.

<Radiometers 20, 21a, and 21b>

First, there will be explained one example of the arrangement of the radiometers 20, 21a, and 21b. In FIG. 2, the case where the direction of an arrow line attached beside a steel material SM is the conveying direction of the steel material SM will be explained as an example. Further, it is set that a scale SC is generated on the surface of the steel material SM.

In FIG. 2, the radiometers 20, 21a, and 21b are arranged so that intersection points between (the surface of) the steel material SM and passing positions of axes of the radiometers 20, 21a, and 21b (optical axes of light-receiving lenses) substantially coincide. Incidentally, in FIG. 2, the case where the radiometers 20, 21a, and 21b are aligned in the conveying direction of the steel material SM is illustrated as an example. However, the radiometers 20, 21a, and 21b do not need to be arranged in this manner as long as the intersection points between (the surface of) the steel material SM and the passing positions of the axes of the radiometers 20, 21a, and 21b (the optical axes of the light-receiving lenses) substantially coincide. For example, the radiometers 20, 21a, and 21b may be aligned in the width direction of the steel material SM.

In the following explanation, the radiometer 20 to be used for measuring the temperature of the steel material is referred to as a radiometer for temperature measurement 20 as necessary. Further, the radiometers 21a and 21b to be used for measuring the spectral emissivity of the steel material are referred to as radiometers for spectral emissivity measurement 21a and 21b as necessary.

Then, there will be explained one example of a wavelength to be detected in the radiometer for temperature measurement 20 and the radiometers for spectral emissivity measurement 21a and 21b. Incidentally, this detected wavelength corresponds to the wavelength $\lambda$ in (1) Equation and (2) Equation.

Wavelengths that can be measured by the radiometer for temperature measurement 20 and the radiometers for spectral emissivity measurement 21a and 21b fall within a band with small absorption by carbon dioxide or water vapor in the atmosphere in a region of 0.6 [μm] to 14.0 [μm] generally.

This lower limit value of 0.6 [μm] is determined by the lower limit value of a wavelength at which the radiometer can measure the spectral radiance. The lower limit value of this wavelength that enables measurement of the spectral radiance is determined according to the temperature of the steel material SM being an object to be measured. When measuring the temperature equal to or more than 900[° C.] as the temperature of the steel material SM being an object to be measured, for example, the lower limit value of the wavelength at which the radiometer can measure the spectral radiance results in 0.6 [μm]. Further, when the lower limit value of the temperature of the steel material SM being an object to be measured is set to 600[° C.], the lower limit value of the detected wavelength results in 0.9 [μm].

Further, the upper limit value of the wavelength being 14.0 [μm] is determined by limiting performance of an optical detector in the radiometer (detection performance of long-wavelength infrared radiation).

Incidentally, a range of the temperature of the steel material SM assumed in this embodiment is 600[° C.] to 1200[° C.].

As above, in this embodiment, the detected wavelength of the radiometer for temperature measurement 20 and the radiometers for spectral emissivity measurement 21a and 21b is preferably selected from within the range of 0.6 [μm] to 14.0 [μm].

Here, there will be explained composition•structure of the scale SC. As has been described in Patent Literature 1, for example, it has been known that as the scale being iron oxide, there are a single-layer scale and a multilayer scale. The single-layer scale is composed only of wustite (FeO). The multilayer scale is composed of wustite (FeO), magnetite ($Fe_3O_4$), and hematite ($Fe_2O_3$). In the multilayer scale, layers of wustite (FeO), magnetite ($Fe_3O_4$), and hematite ($Fe_2O_3$) in order from the base iron side are generated at a thickness ratio of about 94:5:1. FeO, $Fe_3O_4$, and $Fe_2O_3$ each have a peculiar refractive index and attenuation coefficient, so that it is expected that the spectral emissivity being one of optical properties differs between the single-layer scale and the multilayer scale. Thus, the present inventors examined each spectral emissivity of the single-layer scale (the scale SC composed of only FeO) and the multilayer scale (the scale SC in a sandwich structure of $Fe_2O_3$, $Fe_3O_4$, and FeO in order from a surface layer) at two wavelengths of one detected wavelength determined in a region of 3.3 [μm] to 5.0 [μm] (this wavelength is referred to as a wavelength A hereinafter) and the other wavelength determined in a region of 8.0 [μm] to 14.0 [μm] (this wavelength is referred to as a wavelength B hereinafter).

The spectral emissivity was found experimentally as follows.

A steel material specimen with a thermocouple welded thereon is heated in a chamber, and in a state where the steel material specimen is kept to a predetermined temperature, thermal radiance of the steel material specimen is measured by a radiometer. An output L(λ, T) of the radiometer obtained in this manner is read. In the meantime, an indicated temperature of the thermocouple is substituted in (1) Equation to calculate $L_b$(λ, T). Then, the spectral emissivity ε(λ, T) is found from L(λ, T) and $L_b$(λ, T) based on (2) Equation. On this occasion, the single-layer scale and the multilayer scale are formed separately by adjusting the atmosphere in the chamber, and then the spectral emissivity of each scale structure is obtained.

Figure 3A:
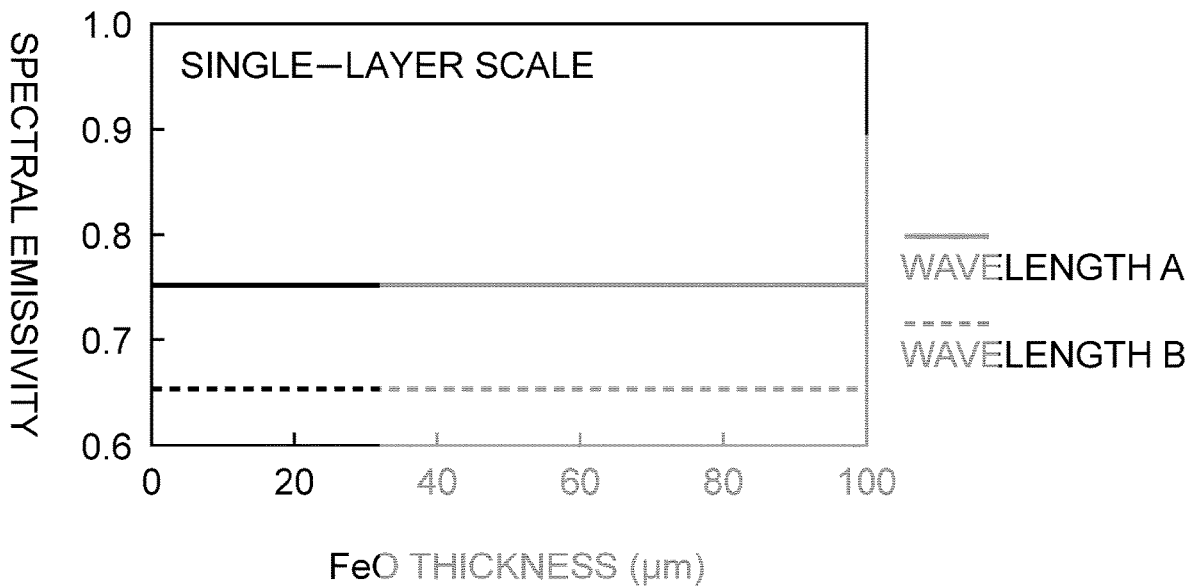
FIG. 3A is a view illustrating one example of the relationship between a thickness of a single-layer scale and spectral emissivity.
Figure 3B:
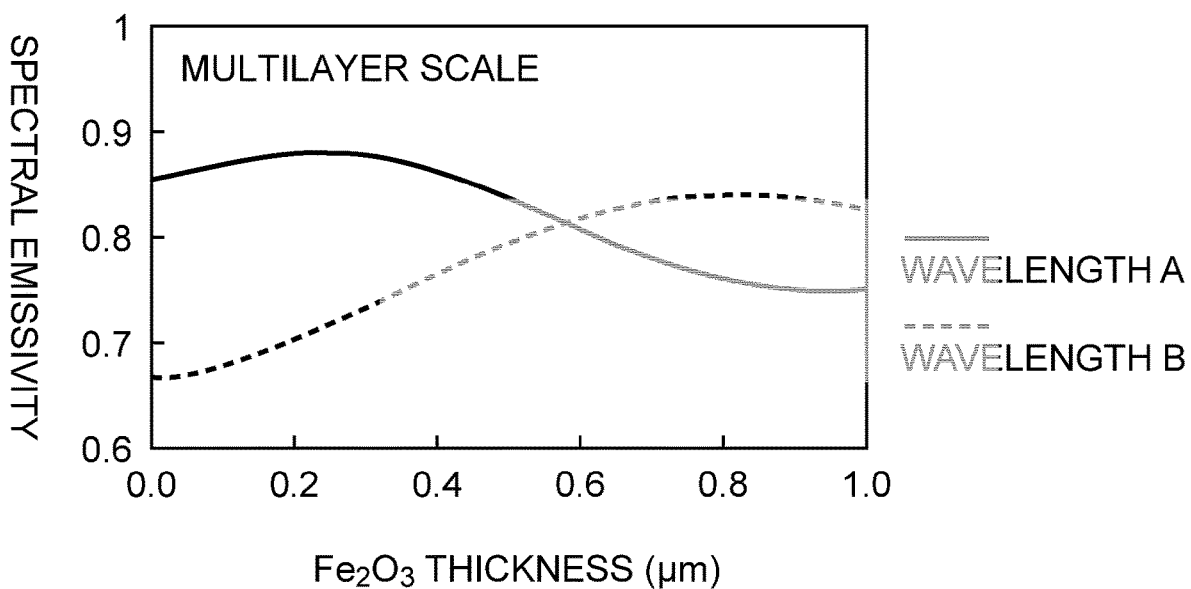
FIG. 3B is a view illustrating one example of the relationship between a thickness of $Fe_2O_3$ generated in the outermost layer of a multilayer scale and spectral emissivity.

FIG. 3A is a view illustrating one example of the relationship between a thickness of the single-layer scale (FeO) and the spectral emissivity. FIG. 3B is a view illustrating one example of the relationship between a thickness of $Fe_2O_3$ generated in the outermost layer of the multilayer scale and the spectral emissivity. In FIG. 3A, the FeO thickness means the (entire) thickness of the single-layer scale. In FIG. 3B, the $Fe_2O_3$ thickness means the thickness of $Fe_2O_3$ generated in the outermost layer of the multilayer scale. As described previously, the thickness of $Fe_2O_3$ generated in the outermost layer of the multilayer scale is about one one-hundredth of the thickness of the entire scale.

As illustrated in FIG. 3A, the spectral emissivity of the single-layer scale indicates a stable value at both the wavelength A and the wavelength B regardless of the thickness of the single-layer scale. This is because FeO is opaque. On the other hand, as illustrated in FIG. 3B, the spectral emissivity of the multilayer scale varies periodically as the thickness of $Fe_2O_3$ changes (namely, $Fe_2O_3$ grows). The period is longer as the wavelength is longer. Incidentally, Patent Literature 1 describes the result of a simulation in which the spectral emissivity of the multilayer scale varies according to the thickness of $Fe_2O_3$ at the wavelength of 3.9 [μm].

The entire thickness of the multilayer scale is larger than the wavelength, but it can be seen that $Fe_2O_3$ has transparency and $Fe_3O_4$ is opaque. Therefore, as described also in Patent Literature 1, an optical interference phenomenon in $Fe_2O_3$ having a thin thickness contributes to the spectral emissivity. Therefore, the spectral emissivity of the multilayer scale varies periodically according to the thickness of $Fe_2O_3$.

Incidentally, it is confirmed separately that the behavior of the spectral emissivity responsive to the thickness of $Fe_2O_3$ generated in the outermost layer of the multilayer scale does not change greatly within the wavelength A or wavelength B range (3.3 [μm] to 5.0 [μm] or 8.0 [μm] to 14.0 [μm]). Here, the behavior of the spectral emissivity responsive to the $Fe_2O_3$ thickness of the surface layer of the multilayer scale means the behavior, for example, at what thickness the value of the spectral emissivity forms a mountain or a valley, whether the spectral emissivity varies monotonously, whether the spectral emissivity has the extreme value, or whether the value of the spectral emissivity is convex upward or convex downward, and means the behavior in a correspondence between the thickness of $Fe_2O_3$ generated in the outermost layer of the multilayer scale and the spectral emissivity.

When the thickness of the entire scale SC is assumed to be up to 100 [μm] (in this case, the thickness of $Fe_2O_3$ becomes about up to 1 [μm]), as is found from FIG. 3A and FIG. 3B, in the case where the spectral emissivity at a single wavelength is observed, the spectral emissivity of $Fe_2O_3$ has a thickness region similar to that of the spectral emissivity of FeO. For example, when the thickness of $Fe_2O_3$ is near 0.8 [μm], the spectral emissivity of $Fe_2O_3$ at the wavelength A results in near 0.75, which is equal to the spectral emissivity of FeO (incidentally, a hundredfold of the thickness of $Fe_2O_3$ is set to the (entire) thickness of the multilayer scale). Accordingly, when the spectral emissivity is measured at a single wavelength, there exists a thickness region where the spectral emissivity fails to determine whether or not $Fe_2O_3$ is present in the outermost layer of the scale SC (namely, whether the scale SC is the single-layer scale or the multilayer scale). Therefore, the present inventors came to employ the following method in this embodiment so as to be able to determine whether the scale SC is the single-layer scale or the multilayer scale in any thickness region.

That is, two wavelengths are selected so as to make the spectral emissivity of $Fe_2O_3$ at least one of these two wavelengths clearly differ from the spectral emissivity of FeO within a thickness range assumed as the thickness of $Fe_2O_3$. This is one of the technical features of this embodiment. Further, the spectral emissivity of $Fe_2O_3$ varies according to the thickness of $Fe_2O_3$. Therefore, the measurement is performed at a plurality of wavelengths so as to prevent the spectral emissivity from becoming a similar value according to the thickness of $Fe_2O_3$. This is also one of the technical features of this embodiment. This will be explained concretely with reference to FIG. 4A and FIG. 4B.

Figure 4A:
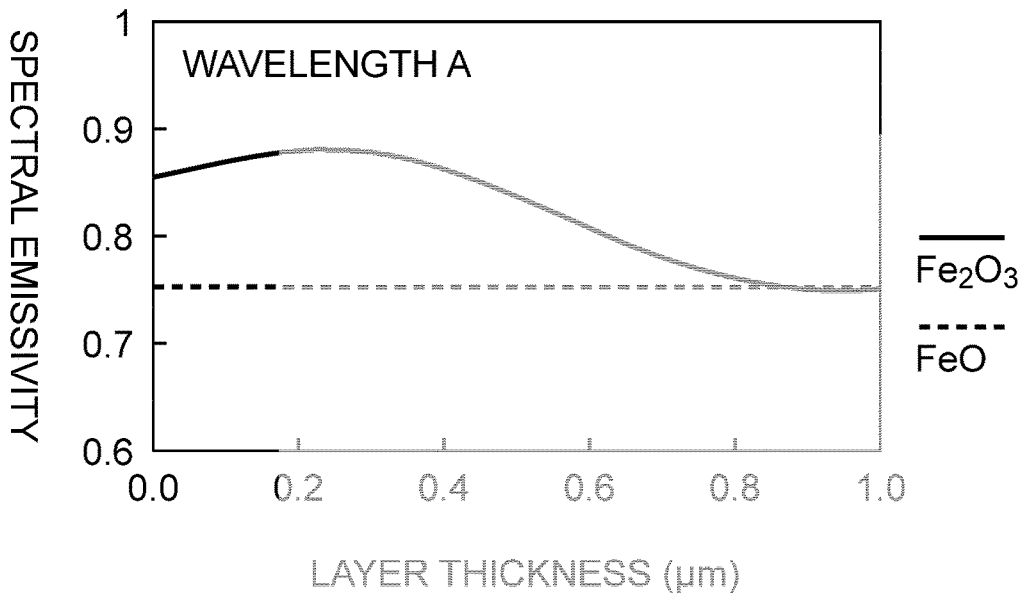
FIG. 4A is a view illustrating the difference between spectral emissivity of the single-layer scale and spectral emissivity of the multilayer scale at a wavelength A.
Figure 4B:
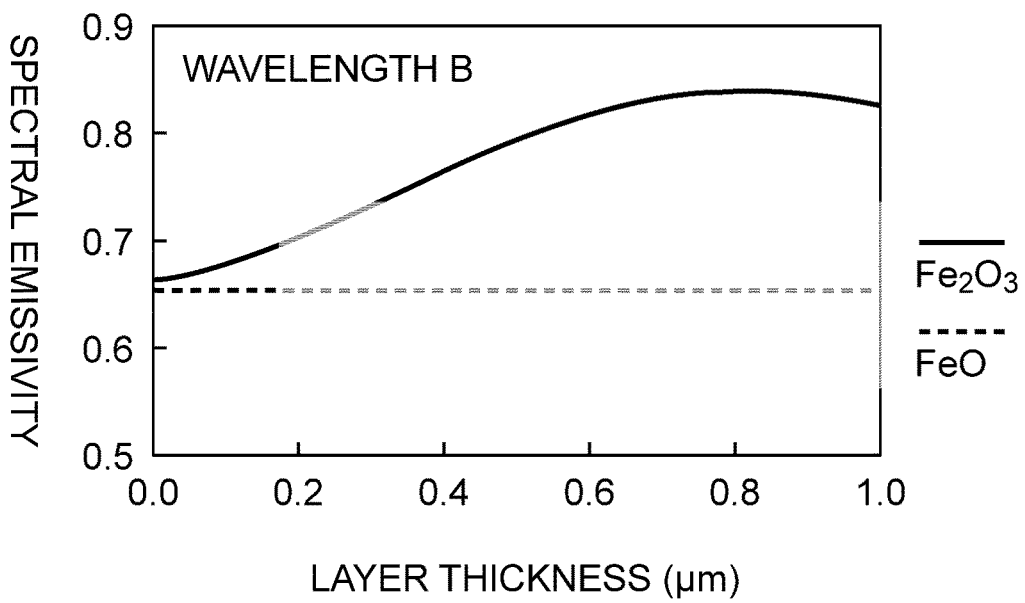
FIG. 4B is a view illustrating the difference between spectral emissivity of the single-layer scale and spectral emissivity of the multilayer scale at a wavelength B.

FIG. 4A is a view illustrating the relationship between a thickness of $Fe_2O_3$ formed in the outermost layer of the multilayer scale and the spectral emissivity of FeO and the spectral emissivity of $Fe_2O_3$ at the wavelength A that is extracted from FIG. 3A and FIG. 3B. FIG. 4B is a view illustrating the relationship between a thickness of $Fe_2O_3$ formed in the outermost layer of the multilayer scale and the spectral emissivity of FeO and the spectral emissivity of $Fe_2O_3$ at the wavelength B that is extracted from FIG. 3A and FIG. 3B. Incidentally, as illustrated in FIG. 3A and FIG. 3B, the spectral emissivity of FeO is fixed regardless of the thickness of the scale SC. On the other hand, the spectral emissivity of the multilayer scale varies periodically according to the thickness of $Fe_2O_3$. In FIG. 4A and FIG. 4B, the layer thickness means the following. That is, the layer thickness corresponds to the (entire) thickness of the single-layer scale with respect to the spectral emissivity of FeO. The layer thickness corresponds to the thickness of $Fe_2O_3$ generated in the outermost layer of the multilayer scale with respect to the spectral emissivity of $Fe_2O_3$.

At the wavelength A illustrated in FIG. 4A, as an example, a "predetermined first range" (see the gray region in the drawing) is set in the range of the spectral emissivity being about 0.7 to 0.8. Then, as long as the measured spectral emissivity is within this predetermined range (see the gray region in the drawing), the scale SC is determined to be FeO. By doing this, the measured spectral emissivity results in a value falling outside the aforementioned predetermined first range in the case of the scale SC, which is an object to be measured, being the multilayer scale as long as the thickness of $Fe_2O_3$ generated in the outermost layer of the multilayer scale is 0.6 [μm] or less. This enables the multilayer scale and the single-layer scale to be distinguished from each other.

In the meantime, at the wavelength B illustrated in FIG. 4B, separately from the "predetermined first range" in the case of the wavelength A illustrated in FIG. 4A, as an example, a "predetermined second range" (see the gray region in the drawing) is set in the range of the spectral emissivity being about 0.6 to 0.7. Then, as long as the measured spectral emissivity is within the predetermined second range, the scale SC is determined to be FeO. By doing this, the measured spectral emissivity results in a value falling outside the aforementioned predetermined second range in the case of the scale SC, which is an object to be measured, being the multilayer scale as long as the thickness of $Fe_2O_3$ generated in the outermost layer of the multilayer scale is 0.2 [μm] or more. This enables the multilayer scale and the single-layer scale to be distinguished from each other.

Incidentally, the aforementioned predetermined first range may be a range including the spectral emissivity of FeO at the wavelength A. Further, the aforementioned predetermined second range may be a range including the spectral emissivity of FeO at the wavelength B. The upper limit value and the lower limit value of the aforementioned predetermined first range and the upper limit value and the lower limit value of the aforementioned predetermined second range each can be set appropriately in consideration of measurement errors (tolerance of the radiometer), and so on.

In the meantime, FIG. 4A reveals that in the case where the thickness of $Fe_2O_3$ generated in the outermost layer of the multilayer scale exceeds 0.6 [μm], the spectral emissivity at the wavelength A results in a value falling within the aforementioned predetermined first range even if the scale SC being an object to be measured is either the single-layer scale or the multilayer scale. Further, FIG. 4B reveals that in the case where the thickness of $Fe_2O_3$ generated in the outermost layer of the multilayer scale goes below 0.2 [μm], the spectral emissivity at the wavelength B results in a value falling within the aforementioned predetermined second range even if the scale SC being an object to be measured is either the single-layer scale or the multilayer scale.

Thus, in this embodiment, the determination in the case of using the wavelength A and the determination in the case of using the wavelength B are combined. Doing this makes it possible to complement the ranges where the determination is impossible at each of the wavelengths A and B independently. Thus, it is possible to distinguish the multilayer scale and the single-layer scale from each other regardless of the thickness of $Fe_2O_3$ generated in the outermost layer of the multilayer scale. That is, as is found from FIG. 4A and FIG. 4B, when at least one of the determination that the spectral emissivity at the wavelength A is out of the aforementioned predetermined first range and the determination that the spectral emissivity at the wavelength B is out of the aforementioned predetermined second range is made, it is possible to determine that $Fe_2O_3$ is present in the outermost layer of the scale SC (that is, the scale SC is the multilayer scale). On the other hand, when the determination that the spectral emissivity at the wavelength A is within the aforementioned predetermined first range and the determination that the spectral emissivity at the wavelength B is within the aforementioned predetermined second range are both made, it is possible to determine that $Fe_2O_3$ is not present in the outermost layer of the scale SC (that is, the scale SC is the single-layer scale).

That is, if the determination illustrated in FIG. 4A is only made, it is impossible to determine whether the scale SC is the multilayer scale or the single-layer scale in the case where the thickness of $Fe_2O_3$ generated in the outermost layer of the scale SC exceeds 0.6 [μm]. On the other hand, if the determination illustrated in FIG. 4B is only made, it is impossible to determine whether the scale SC is the multilayer scale or the single-layer scale in the case where the thickness of $Fe_2O_3$ generated in the outermost layer of the scale SC goes below 0.2 [μm]. Thus, combining these determinations reveals that in the case where $Fe_2O_3$ has been generated in the outermost layer of the scale SC, the value of the spectral emissivity falls outside the aforementioned predetermined first range or the aforementioned predetermined second range at at least one of the determination at the wavelength A and the determination at the wavelength B. Accordingly, it becomes possible to easily determine whether the scale SC is the multilayer scale or the single-layer scale regardless of the thickness of $Fe_2O_3$ generated in the outermost layer of the multilayer scale.

As above, the wavelengths A and B are determined to make the spectral emissivity of $Fe_2O_3$ at at least one of the wavelength A and the wavelength B fall outside a predetermined range set at the corresponding wavelength at any thickness of $Fe_2O_3$. Here, the predetermined range set at the wavelength A is the aforementioned predetermined first range. The predetermined range set at the wavelength B is the aforementioned predetermined second range. Incidentally, in FIG. 4A and FIG. 4B, the case where the range of 0.0 [μm] to 1.0 [μm] is assumed as the thickness of $Fe_2O_3$ is illustrated as an example. The range of the thickness of $Fe_2O_3$ is found as follows, for example. First, by using the temperature of the steel material SM when the scale is removed by descaling and an elapsed time thereafter, the range of the thickness of the entire scale SC is found from a well-known scale thickness equation. The scale thickness equation is an equation to find the entire thickness of the scale SC from a function of temperature and time. Then, as the range of the thickness of $Fe_2O_3$ assumed to be generated in the hot rolling line, thicknesses of 1[%] of the upper limit value and the lower limit value of the range of the entire thickness of the scale SC are found. Further, the range of the thickness of $Fe_2O_3$ may be found by performing a laboratory experiment of scale generation assuming actual temperature history, for example.

Next, there will be explained one example of a method of measuring the temperature T of the steel material SM necessary for finding the spectral emissivity.

It is not practical to use a contact-type thermometer such as a thermocouple at the time of online measurement in the hot rolling line illustrated in FIG. 1. This is because the thermometer is liable to be broken. Thus, in this embodiment, the temperature of the steel material SM is measured by radiation thermometry. At the time of radiation temperature measurement, the spectral emissivity is desired to be already known and fixed. However, the scale SC is expected that the spectral emissivity varies in any wavelength band due to the composition or optical interference. Thus, in this embodiment, the radiation temperature measurement is performed in a short-wavelength band. On the other hand, the spectral emissivity is measured in an infrared long-wavelength band.

Figure 5:
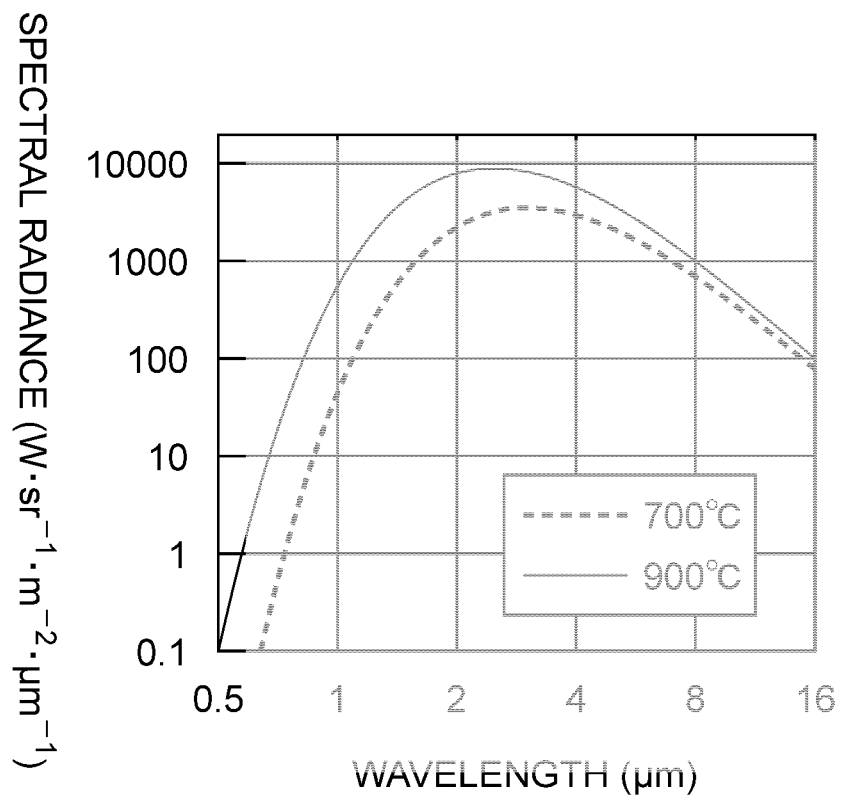
FIG. 5 is a view illustrating one example of the relationship between spectral radiance of a blackbody and a wavelength.

This reason will be explained as follows. FIG. 5 is a view illustrating one example of the relationship between the spectral radiance $L_b(\lambda, T)$ of the blackbody and a wavelength. In FIG. 5, the relationships in the case of the temperature T of the blackbody=700[° C.] and 900[° C.] are illustrated as an example. The curves illustrated in FIG. 5 are calculated from a theoretical formula of blackbody radiation (Planck's law of radiation).

As is clear from FIG. 5, the change in the spectral radiance according to the temperature T is larger in a short-wavelength region than in the region near about 2 [μm]. Accordingly, in the short-wavelength region, temperature measurement relatively robust against the variation in the spectral emissivity is enabled, which is suitable for the measurement of temperature. On the other hand, as is clear from FIG. 5, the change in the spectral radiance according to the temperature T is smaller in a long-wavelength region than in the region near about 4 [μm]. Accordingly, in the long-wavelength region, measurement relatively robust against the variation in the temperature is enabled, which is suitable for the measurement of spectral emissivity.

As the radiometer for temperature measurement at the short wavelength, wavelengths of 0.65 [μm], 0.9 [μm], and 1.55 [μm] are mainly used as the detected wavelength generally. A shorter detected wavelength makes the temperature measurement error caused by the variation in emissivity smaller. However, the radiometer with the detected wavelength being 0.65 [μm] is limited to the temperature measurement of an object to be measured at a high temperature of about 900[° C.] or more. Therefore, the case of using the radiometer with the detected wavelength of 0.9 [μm] will be explained here as an example.

The following was performed in order to confirm that the variation in the spectral emissivity at the wavelength $\lambda=0.9$ [μm] at which radiation temperature measurement is performed does not prevent the measurement of the spectral emissivities at the wavelength A and the wavelength B. Incidentally, the variation in the spectral emissivity means the difference between the spectral emissivity set when performing the radiation temperature measurement and the actual spectral emissivity.

When the spectral emissivity of FeO at the wavelength of 0.9 [μm] was found experimentally, the result was about 0.78 stably. On the other hand, when the spectral emissivity of $Fe_2O_3$ at this wavelength was measured, the result varied unstably in a range of 0.78±0.07. This variation in the spectral emissivity of $Fe_2O_3$ is inferred to be caused by an optical interference phenomenon in a $Fe_2O_3$ film (in a layer). When the spectral emissivity of the radiometer is set to 0.78 and the temperature of the object to be measured with the temperature T=900° C. is measured, a temperature measurement error of about ±8[° C.] is generated by the variation in the spectral emissivity of ±0.07.

Figure 6A:
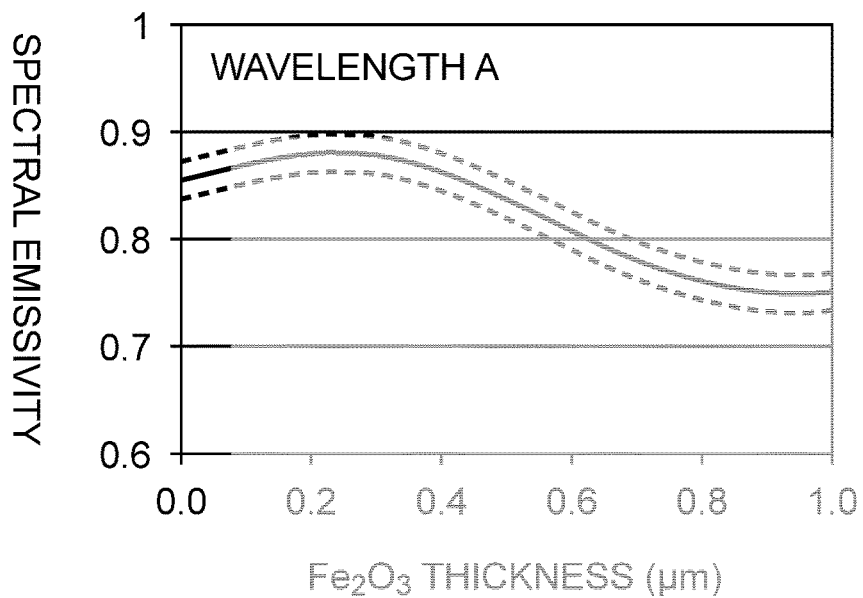
FIG. 6A is a view illustrating one example of the relationship between a thickness of $Fe_2O_3$ generated in the outermost layer of the multilayer scale and spectral emissivity of $Fe_2O_3$ at the wavelength A.
Figure 6B:
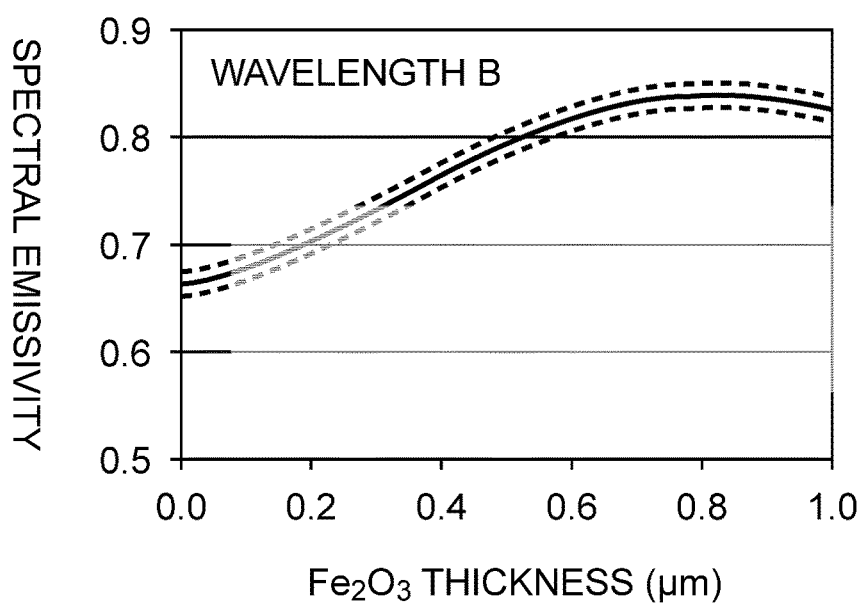
FIG. 6B is a view illustrating one example of the relationship between a thickness of $Fe_2O_3$ generated in the outermost layer of the multilayer scale and spectral emissivity of $Fe_2O_3$ at the wavelength B.

With reference to FIG. 6A and FIG. 6B, there will be explained an effect of the temperature measurement error on the spectral emissivity of $Fe_2O_3$. FIG. 6A is a view illustrating one example of the relationship between a thickness of $Fe_2O_3$ generated in the outermost layer of the multilayer scale and the spectral emissivity of $Fe_2O_3$ at the wavelength A. FIG. 6B is a view illustrating one example of the relationship between a thickness of $Fe_2O_3$ generated in the outermost layer of the multilayer scale and the spectral emissivity of $Fe_2O_3$ at the wavelength B. In FIG. 6A and FIG. 6B, the $Fe_2O_3$ thickness means the thickness of $Fe_2O_3$ generated in the outermost layer of the multilayer scale.

In FIG. 6A and FIG. 6B, the curves indicated by a solid line are the ones illustrated in FIG. 4A and FIG. 4B. Due to the previously described temperature measurement error of ±8[° C.], uncertainty in a curve range indicated by a dotted line in each of FIG. 6A and FIG. 6B is generated relative to this curve indicated by a solid line in terms of the spectral emissivity. No problem is caused in terms of the previously described determination of the composition of the scale even if such uncertainty of the temperature measurement is generated. That is, as described previously, it is determined whether or not the spectral emissivity at the wavelength A and the spectral emissivity at the wavelength B fall within the aforementioned predetermined first range and the aforementioned predetermined second range (the gray regions illustrated in FIG. 4A and FIG. 4B) respectively. On this occasion, even if the uncertainty in a curve range indicated by a dotted line in each of FIG. 6A and FIG. 6B is generated, at least one of the fact that the spectral emissivity at the wavelength A falls outside the aforementioned predetermined first range and the fact that the spectral emissivity at the wavelength B falls outside the aforementioned predetermined second range occurs as long as the outermost layer of the scale SC is $Fe_2O_3$.

From the above, in this embodiment, the detected wavelength of the radiometer for temperature measurement 20 is preferably set to 0.9 [μm]. As a detector in the radiometer for temperature measurement 20 for the spectral radiance, it is preferred to use a silicon detector, for example. Further, as described previously, the spectral emissivity of $Fe_2O_3$ at the wavelength λ=0.9 [μm] varies in the range of 0.78±0.07. Thus, in this embodiment, as spectral emissivity $\varepsilon_{TH}$ to be used for deriving the temperature T of the steel material SM, using 0.78 is considered.

On the other hand, the detected wavelength of the radiometer for spectral emissivity measurement 21a is set to the wavelength A falling within a range of 3.3 [μm] to 5.0 [μm]. Further, the detected wavelength of the radiometer for spectral emissivity measurement 21b is set to the wavelength B falling within a range of 8.0 [μm] to 14.0 [μm]. The radiometer for spectral emissivity measurement 21a can be fabricated by attaching an optical filter to a radiometer having, for example, an MCT (HgCdTe) detector as a detector. Further, the radiometer for spectral emissivity measurement 21b can be fabricated by attaching an optical filter to a radiometer having, for example, a pyroelectric detector as a detector. These radiometers (the radiometer for temperature measurement 20 and the radiometers for spectral emissivity measurement 21a and 21b) can stably measure thermal radiation as long as the temperature of an object to be measured is 600[° C.] or more.

<Scale Composition Determination Device 10>

Next, there will be explained one example of details of the scale composition determination device 10. Hardware of the scale composition determination device 10 can be fabricated by using an information processing device including a CPU, a ROM, a RAM, a HDD, and various interfaces or using dedicated hardware, for example.

FIG. 7 is a flowchart explaining one example of the operation of the scale composition determination device 10. There will be explained one example of the function of the scale composition determination device 10 with reference to FIG. 2 and FIG. 7. Incidentally, the flowchart in FIG. 7 is executed every time the spectral radiance of the steel material SM is detected by the radiometer for temperature measurement 20 and the radiometers for spectral emissivity measurement 21a and 21b.

At Step S701, a spectral radiance acquisition unit 201 acquires the spectral radiances of the steel material SM detected by the radiometer for temperature measurement 20 and the radiometers for spectral emissivity measurement 21a and 21b.

Next, at Step S702, a temperature deriving unit 202 calculates (3) Equation below, to thereby derive the temperature T of the steel material SM.

[Mathematical equation 3]

[Mathematical equation 3]

$$L_{TH} = \varepsilon_{TH} \times \frac{2c_1}{\lambda_{TH}^5} \frac{1}{\exp\left(\frac{c_2}{\lambda_{TH} \times T}\right) - 1} \quad (3)$$

Here, $\lambda_{TH}$ is the detected wavelength of the radiometer for temperature measurement 20. $L_{TH}$ is the spectral radiance of the steel material SM detected by the radiometer for temperature measurement 20. The spectral radiance $L_{TH}$ of the steel material SM is the one acquired at Step S701. Further, $\varepsilon_{TH}$ is the spectral emissivity to be used when deriving the temperature T of the steel material SM. As described previously, in this embodiment, 0.78 can be used as the spectral emissivity $\varepsilon_{TH}$.

Next, at Step S703, a spectral emissivity deriving unit 203 calculates (4) Equation and (5) Equation below, to thereby derive spectral emissivity $\varepsilon_A$ and spectral emissivity $\varepsilon_B$ at the wavelength A ($\lambda_A$ in (4) Equation) and the wavelength B ($\lambda_B$ in (5) Equation).

[Mathematical equation 4]

[Mathematical equation 4]

$$\varepsilon_A = \frac{L_A}{\frac{2c_1}{\lambda_A^5} \frac{1}{\exp\left(\frac{c_2}{\lambda_A \times T}\right) - 1}} \quad (4)$$

$$\varepsilon_B = \frac{L_B}{\frac{2c_1}{\lambda_B^5} \frac{1}{\exp\left(\frac{c_2}{\lambda_B \times T}\right) - 1}} \quad (5)$$

Here, T is the temperature of the steel material SM derived at Step S702. $L_A$ is the spectral radiance of the steel material SM detected by the radiometer for spectral emissivity measurement 21a. $L_B$ is the spectral radiance of the steel material SM detected by the radiometer for spectral emissivity measurement 21b. These spectral radiances $L_A$ and $L_B$ of the steel material SM are the ones acquired at Step S701.

Next, at Step S704, a determination unit 204 determines whether or not the spectral emissivity $\varepsilon_A$ at the wavelength A is within the aforementioned predetermined first range. As described previously, in this embodiment, the aforementioned predetermined first range is from 0.70 to 0.80 (see FIG. 4A).

As a result of this determination, in the case where the spectral emissivity $\varepsilon_A$ at the wavelength A is not within the aforementioned predetermined first range, it is determined that $Fe_2O_3$ has been generated in the outermost layer of the scale SC (namely, it is determined that the multilayer scale has been generated on the surface of the steel material SM). Then, at Step S705, an output unit 205 outputs information indicating that $Fe_2O_3$ has been generated in the outermost layer of the scale SC (the multilayer scale has been generated on the surface of the steel material SM). Then, the processing by the flowchart in FIG. 7 is finished.

On the other hand, at Step S704, in the case where it is determined that the spectral emissivity $\varepsilon_A$ at the wavelength A is within the aforementioned predetermined first range, the processing proceeds to Step S706. When proceeding to Step S706, the determination unit 204 determines whether or not the spectral emissivity $\varepsilon_B$ at the wavelength B is within the aforementioned predetermined second range. As described previously, in this embodiment, the aforementioned predetermined second range is from 0.60 to 0.70 (see FIG. 4B).

As a result of this determination, in the case where the spectral emissivity $\varepsilon_B$ at the wavelength B is not within the aforementioned predetermined second range, it is determined that $Fe_2O_3$ has been generated in the outermost layer of the scale SC (namely, it is determined that the multilayer scale has been generated on the surface of the steel material SM). Then, at Step S705, the output unit 205 outputs information indicating that $Fe_2O_3$ has been generated in the outermost layer of the scale SC (the multilayer scale has been generated on the surface of the steel material SM). Then, the processing by the flowchart in FIG. 7 is finished.

On the other hand, at Step S706, in the case where it is determined that the spectral emissivity at the wavelength B is within the aforementioned predetermined second range, it is determined that $Fe_2O_3$ has not been generated in the outermost layer of the scale SC (namely, it is determined that the single-layer scale has been generated on the surface of the steel material SM). Then, at Step S707, the output unit 205 outputs information indicating that $Fe_2O_3$ has not been generated in the outermost layer of the scale SC (the single-layer scale has been generated on the surface of the steel material SM). Then, the processing by the flowchart in FIG. 7 is finished.

Incidentally, as a mode of outputting the aforementioned information by the output unit 205, it is possible to employ at least one of displaying it on a computer display, transmitting it to an external device, and storing it in an internal or external storage medium of the scale composition determination device 10, for example.

Figure 8:
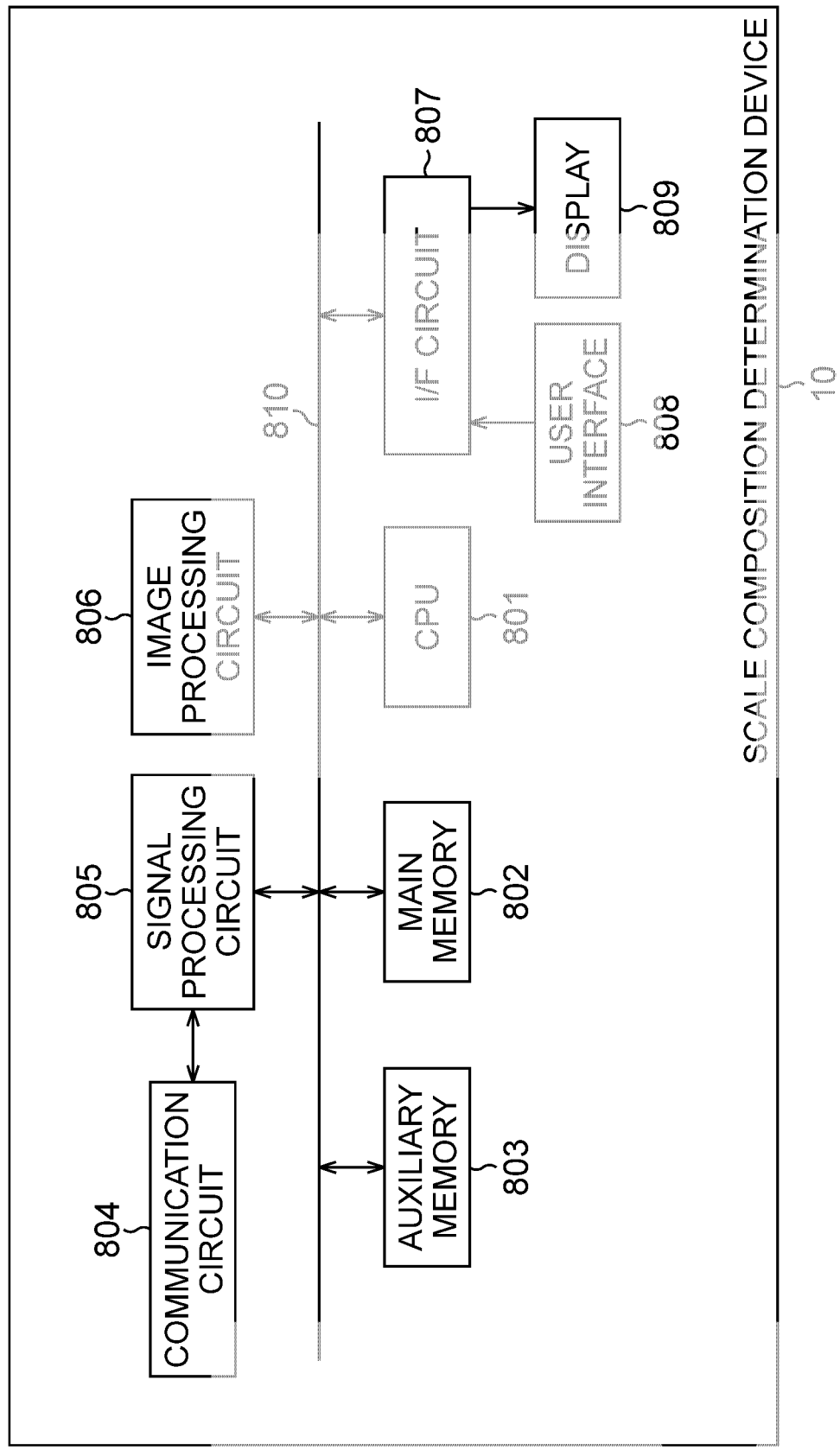
FIG. 8 is a diagram illustrating one example of a hardware configuration of the scale composition determination device.

FIG. 8 is a diagram illustrating one example of a configuration of the hardware of the scale composition determination device 10.

In FIG. 8, the scale composition determination device 10 includes a CPU 801, a main memory 802, an auxiliary memory 803, a communication circuit 804, a signal processing circuit 805, an image processing circuit 806, an I/F circuit 807, a user interface 808, a display 809, and a bus 810.

The CPU 801 integrally controls the whole of the scale composition determination device 10. The CPU 801 uses the main memory 802 as a work area to execute programs stored in the auxiliary memory 803. The main memory 802 stores data temporarily. The auxiliary memory 803 stores various pieces of data other than the programs to be executed by the CPU 801. The auxiliary memory 803 stores pieces of information necessary for the processing of the flowchart illustrated in FIG. 7, which are the previously described predetermined first range, predetermined second range, and so on.

The communication circuit 804 is a circuit for performing communication with the outside of the scale composition determination device 10.

The signal processing circuit 805 performs various pieces of signal processing on a signal received in the communication circuit 804 and a signal input in accordance with the control by the CPU 801. The spectral radiance acquisition unit 201 exhibits its function by using the CPU 801, the communication circuit 804, and the signal processing circuit 805, for example. Further, the temperature deriving unit 202, the spectral emissivity deriving unit 203, and the determination unit 204 exhibit their functions by using the CPU 801 and the signal processing circuit 805, for example.

The image processing circuit 806 performs various pieces of image processing on a signal input in accordance with the control by the CPU 801. The image-processed signal is output to the display 809.

The user interface 808 is a part through which an operator gives an instruction to the scale composition determination device 10. The user interface 808 includes, for example, buttons, switches, dials, and so on. Further, the user interface 808 may have a graphical user interface using the display 809.

The display 809 displays an image based on a signal output from the image processing circuit 806. The I/F circuit 807 exchanges data with devices connected to the I/F circuit 807. In FIG. 8, as the device connected to the I/F circuit 807, the user interface 808 and the display 809 are illustrated. However, the device connected to the I/F circuit 807 is not limited to these. For example, a portable storage medium may be connected to the I/F circuit 807. Further, at least a part of the user interface 808 and the display 809 may be provided outside the scale composition determination device 10.

The output unit 205 exhibits its function by using at least one of a pair of the communication circuit 804 and the signal processing circuit 805 and a pair of the image processing circuit 806, the I/F circuit 807, and the display 809, for example.

Incidentally, the CPU 801, the main memory 802, the auxiliary memory 803, the signal processing circuit 805, the image processing circuit 806, and the I/F circuit 807 are connected to the bus 810. Communications between these components are performed through the bus 810. Further, the hardware of the scale composition determination device 10 is not limited to the one illustrated in FIG. 8 as long as the previously described functions of the scale composition determination device 10 can be achieved.

In this embodiment as above, the scale composition determination device 10 determines that $Fe_2O_3$ has been generated in the outermost layer of the scale SC in the case where at least one of the spectral emissivity at the wavelength A and the spectral emissivity at the wavelength B that are measured by the radiometers for spectral emissivity measurement 21a and 21b is not within a predetermined range set at each of the wavelength A and the wavelength B, and determines that $Fe_2O_3$ has not been generated in the outermost layer of the scale SC in the case where all the spectral emissivity at the wavelength A and the spectral emissivity at the wavelength B that are measured by the radiometers for spectral emissivity measurement 21a and 21b is within a predetermined range set at each of the wavelength A and the wavelength B. Here, in the predetermined ranges set at the wavelength A and the wavelength B respectively (the aforementioned predetermined first range and the aforementioned predetermined second range), the spectral emissivity of FeO at the wavelength A and the spectral emissivity of FeO at the wavelength B are included. Accordingly, spectral radiances at different wavelengths are detected, thereby making it possible to accurately determine whether the scale SC generated on the surface of the steel material SM during operation is the single-layer scale or the multilayer scale online. This makes it possible to perform operational management speedily and accurately and reflect a determination result of the composition of the scale SC in the operation speedily and accurately, for example.

MODIFIED EXAMPLE

Modified Example 1

In this embodiment, the case where the detected wavelength of the radiometer for temperature measurement 20 is 0.9 [μm] has been explained as an example. However, as the detected wavelength of the radiometer for temperature measurement 20, a wavelength of 2.0 [μm] or less can be employed based on the result illustrated in FIG. 5. Incidentally, the same thing as that explained with reference to FIG. 6A and FIG. 6B can be said even if the detected wavelength of the radiometer for temperature measurement 20 is set to 1.6 [μm], for example. That is, even when the uncertainty is generated in the spectral emissivities measured by the radiometers for spectral emissivity measurement 21a and 21b due to the temperature measurement error by the radiometer for temperature measurement 20, the spectral emissivity of $Fe_2O_3$ at at least one of the wavelengths falls outside the aforementioned predetermined range set at the corresponding wavelength. Further, as in this embodiment, when the number of wavelengths for finding the spectral emissivity is set to two, it is possible to reduce the number of radiometers. Further, it is possible to simplify the processing. However, the number of wavelengths for finding the spectral emissivity may be three or more. Even in this case, as illustrated in FIG. 4A and FIG. 4B, a plurality of wavelengths and corresponding predetermined ranges are determined to make the spectral emissivity of $Fe_2O_3$ at at least one wavelength out of a plurality of the wavelengths fall outside the predetermined range set at the corresponding wavelength within a range of the thickness assumed as the thickness of $Fe_2O_3$. As described previously, it is designed so that in a predetermined range set at each of a plurality of the wavelengths, the spectral emissivity of FeO at the corresponding wavelength is included.

Modified Example 2

In this embodiment, the case of using the three radiometers 20, 21a, and 21b has been explained as an example. However, this embodiment does not necessarily need to be configured in this manner as long as it is designed to detect spectral radiances at at least three different wavelengths. For example, light that has entered through the same light collecting lens is divided into three by half mirrors. Then, the divided light is made to pass through one of three wavelength selecting filters through which only lights with wavelengths different from one another pass. Spectral radiance of the light that has passed through the wavelength selecting filter is detected. In this manner, space saving of the radiometers can be achieved.

Modified Example 3

In this embodiment, the case where a set of the radiometers 20, 21a, and 21b is arranged in a region between the descaler 12b and the rolling stand 14b provided on the most upstream side out of the rolling stands having work rolls and backup rolls has been explained as an example. However, the place where a set of the radiometers is arranged is not limited to this place as long as it is a place on the downstream side from the descaler 12a on the most upstream side in the hot rolling process (the temperature of the steel sheet that has been extracted from the heating furnace 11 to be subjected to descaling at least one time is measured). It is possible to arrange a set of radiometers in a place between a descaler and a rolling stand located closest to the descaler on the downstream side, for example. Further, each set of radiometers may be arranged at a plurality of locations in such a place (that is, a plurality of sets of radiometers may be arranged). In this case, the scale composition determination device 10 performs the processing by the flowchart illustrated in FIG. 7 using each of the sets of radiometers and determines whether or not $Fe_2O_3$ has been generated in the outermost layer of the scale SC in each place where the set of radiometers is arranged.

Modified Example 4

In this embodiment, the case where the scale composition determination device 10 is applied to the hot rolling line has been explained as an example. However, the application destination of the scale composition determination device 10 is not limited to the hot rolling line. The scale composition determination device 10 may be applied to the heating furnace described in Patent Literature 1, for example. Even in this case, as illustrated in FIG. 4A and FIG. 4B, a plurality of wavelengths and corresponding predetermined ranges are determined to make the spectral emissivity of $Fe_2O_3$ at at least one wavelength out of a plurality of the wavelengths fall outside the predetermined range set at the corresponding wavelength within a range of the thickness assumed as the thickness of $Fe_2O_3$. As described previously, it is designed so that in a predetermined range set at each of a plurality of the wavelengths, the spectral emissivity of FeO at the corresponding wavelength is included.

Modified Example 5

In this embodiment, the case of measuring the temperature of the steel material SM by using the radiometer 20 has been explained as an example. However, it is not necessarily to find the temperature of the steel material SM by using the radiometer 20. The temperature of the steel material SM may be derived online by performing a heat-transfer calculation, for example. Further, in the case where the temperature of the steel material SM can be obtained accurately from the past operation performance, the obtained temperature of the steel material SM may be used. Unless there is a risk of damage in a thermometer, a contact-type thermometer may be used.

Modified Example 6

As long as it is determined whether or not the spectral emissivities at a plurality of wavelengths are within predetermined ranges set at a plurality of the wavelengths respectively as in this embodiment, it is preferred because it is possible to determine whether or not $Fe_2O_3$ has been generated in the outermost layer of the scale SC regardless of the temperature of the steel material easily and highly accurately. However, the spectral emissivities do not necessarily need to be found under such a condition that the temperature of the steel material is kept to a substantially fixed predetermined temperature. In this case, for example, it is only necessary to determine whether or not the spectral radiances at a plurality of wavelengths are within predetermined ranges set at a plurality of the wavelengths respectively. In this case as well, in the same manner as in the explanation made with reference to FIG. 4A and FIG. 4B, a plurality of wavelengths and corresponding predetermined ranges are determined to make the spectral radiance of $Fe_2O_3$ at at least one wavelength out of a plurality of the wavelengths fall outside the predetermined range set at the corresponding wavelength within a range of the thickness assumed as the thickness of $Fe_2O_3$. Further, it is designed so that in a predetermined range set at each of a plurality of the wavelengths, the spectral radiance of FeO at the corresponding wavelength is included.

Other Modified Examples

Incidentally, the above-explained embodiment of the present invention can be implemented by causing a computer to execute a program. Further, a computer-readable recording medium in which the aforementioned program is recorded and a computer program product such as the aforementioned program are also applicable as the embodiment of the present invention. As the recording medium, for example, a flexible disk, a hard disk, an optical disk, a magnetic optical disk, a CD-ROM, a magnetic tape, a nonvolatile memory card, a ROM, or the like can be used.

It should be noted that the above embodiments merely illustrate concrete examples of implementing the present invention, and the technical scope of the present invention is not to be construed in a restrictive manner by these embodiments. That is, the present invention may be implemented in various forms without departing from the technical spirit or main features thereof.

INDUSTRIAL APPLICABILITY

The present invention can be utilized for manufacturing a steel material, and so on.

The invention claimed is:

1. A scale composition determination system that determines a composition of a scale generated on a surface of a steel material, the scale composition determination system comprising:
   a computer processor including processing circuitry that:
   derives spectral emissivity of the steel material at each of a plurality of wavelengths based on a temperature of the steel material and spectral radiance of the steel material at each of a plurality of the wavelengths; and
   determines whether or not hematite ($Fe_2O_3$) has been generated in an outermost layer of the scale based on the spectral emissivity of the steel material at each of a plurality of the wavelengths, wherein
   the computer processor determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths,
   in the predetermined range set at the wavelength, spectral emissivity of wustite (FeO) at the corresponding wavelength is included,
   a plurality of the wavelengths are determined by using the relationship between the spectral emissivity of the hematite at each of a plurality of the wavelengths and a thickness of the hematite within a range assumed as the thickness of the hematite, and
   a plurality of the wavelengths are determined to make the spectral emissivity of the hematite at at least one wavelength of a plurality of the wavelengths fall outside the predetermined range set at the corresponding wavelength at any thickness of the hematite in the relationship.

2. The scale composition determination system according to claim 1, wherein
   a plurality of the wavelengths include a wavelength selected from a wavelength band of 3.3 [μm] to 5.0 [μm] and a wavelength selected from a wavelength band of 8.0 [μm] to 14.0 [μm].

3. A scale composition determination method that determines a composition of a scale generated on a surface of a steel material, the scale composition determination method comprising:
   a detection step of detecting spectral radiance of the steel material at each of a plurality of wavelengths;
   a temperature acquisition step of acquiring a temperature of the steel material;
   a spectral emissivity deriving step of deriving spectral emissivity of the steel material at each of a plurality of the wavelengths based on the temperature of the steel material acquired by the temperature acquisition step and the spectral radiance of the steel material at each of a plurality of the wavelengths, the spectral radiance detected by the detection step; and
   a determination step of determining whether or not hematite ($Fe_2O_3$) has been generated in an outermost layer of the scale based on the spectral emissivity of the steel material at each of a plurality of the wavelengths, the spectral emissivity derived by the spectral emissivity deriving step, wherein
   the determination step determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths,
   in the predetermined range set at the wavelength, spectral emissivity of wustite (FeO) at the corresponding wavelength is included,
   a plurality of the wavelengths are determined by using the relationship between the spectral emissivity of the hematite at each of a plurality of the wavelengths and a thickness of the hematite within a range assumed as the thickness of the hematite, and
   a plurality of the wavelengths are determined to make the spectral emissivity of the hematite at at least one wavelength of a plurality of the wavelengths fall outside the predetermined range set at the wavelength at any thickness of the hematite in the relationship.

4. A non-transitory computer-readable storage medium recording a program, executable by a computer processor including processing circuitry, for causing a computer to execute determination of a composition of a scale generated on a surface of a steel material, the program causing a computer to execute:
   a spectral emissivity deriving step of deriving spectral emissivity of the steel material at each of a plurality of wavelengths based on a temperature of the steel material and spectral radiance of the steel material at each of a plurality of the wavelengths; and
   a determination step of determining whether or not hematite ($Fe_2O_3$) has been generated in an outermost layer of the scale based on the spectral emissivity of the steel material at each of a plurality of the wavelengths, the spectral emissivity derived by the spectral emissivity deriving step, wherein
   the determination step determines that the hematite ($Fe_2O_3$) has been generated in the outermost layer of the scale in the case where at least one of the spectral emissivities of the steel material at a plurality of the wavelengths is out of a predetermined range set at each of a plurality of the wavelengths, and determines that the hematite ($Fe_2O_3$) has not been generated in the outermost layer of the scale in the case where all of the spectral emissivities of the steel material at a plurality of the wavelengths is within the predetermined range set at each of a plurality of the wavelengths,
   in the predetermined range set at the wavelength, spectral emissivity of wustite (FeO) at the corresponding wavelength is included,
   a plurality of the wavelengths are determined by using the relationship between the spectral emissivity of the hematite at each of a plurality of the wavelengths and a thickness of the hematite within a range assumed as the thickness of the hematite, and a plurality of the wavelengths are determined to make the spectral emissivity of the hematite at at least one wavelength of a plurality of the wavelengths fall outside the predetermined range set at the wavelength at any thickness of the hematite in the relationship.

\* \* \* \* \*